United States Patent [19]

DeVries

[11] 4,140,409
[45] Feb. 20, 1979

[54] DISPOSABLE LIQUID APPLICATOR

[75] Inventor: James H. DeVries, McHenry, Ill.

[73] Assignee: Baxter Travenol Laboratories, Inc., Deerfield, Ill.

[21] Appl. No.: 830,168

[22] Filed: Sep. 2, 1977

[51] Int. Cl.² .............................................. A47L 13/17
[52] U.S. Cl. ..................................... 401/132; 128/269; 401/196
[58] Field of Search ............... 401/132, 133, 183, 196; 128/269, 260, 261; 206/531, 828, 620, 634

[56] References Cited

U.S. PATENT DOCUMENTS

| | | | |
|---|---|---|---|
| 3,369,267 | 2/1968 | Friedland et al. | 401/132 X |
| 3,386,793 | 6/1968 | Stanton | 401/132 |
| 3,635,567 | 1/1972 | Richardson | 401/196 X |
| 3,647,305 | 3/1972 | Baker et al. | 401/132 X |
| 3,689,458 | 9/1972 | Hellstrom | 206/531 X |
| 3,741,384 | 6/1973 | Cloud | 206/634 X |
| 3,759,259 | 9/1973 | Truhan | 128/269 |
| 3,998,559 | 12/1976 | Hoyt | 401/132 |

Primary Examiner—Ronald E. Suter
Attorney, Agent, or Firm—Henry W. Collins; George H. Gerstman; Paul C. Flattery

[57] ABSTRACT

A disposable liquid applicator is provided in which the liquid to be dispensed is carried within a prescored container. Absorbent material is fastened to the container overlying the prescored portion. The container and the absorbent material cooperate to cause the liquid to be dispensed into the absorbent material when the container is bent away from the prescored portion and about itself.

10 Claims, 6 Drawing Figures

DISPOSABLE LIQUID APPLICATOR

BACKGROUND OF THE INVENTION

This invention relates to an improved disposable liquid applicator.

In many medical procedures, medicines or scrubbing materials must be applied to parts of the body, such as the skin. For example, in the preparation of a sterile phlebotomy site, absorbent or swab material is impregnated with the necessary chemicals for sterilization combined with the necessary scrubbing materials, with the liquid then being applied to the skin at the site. Prior art disposable scrubbing devices have been proposed, generally utilizing frangible ampoules or capsules, such as disclosed in Avery U.S. Pat. No. 3,891,331, Bailey U.S. Pat. No. 3,826,259, Arcudi U.S. Pat. No. 3,466,131, Lewis U.S. Pat. No. 3,060,486 and Avery U.S. Pat. No. 3,768,916.

I have discovered that an effective scrubbing device which is capable of low cost, high volume production can be provided without the necessity of using frangible ampoules or capsules carried by a receptacle-portion of the device. To this end, it is an object of the invention to eliminate the need for a frangible ampoule or capsule carried by the receptacle-portion of the device.

Another object of the invention is to provide a disposable liquid applicator, the body of which comprises a container that is prescored and is covered with a seal. Absorbent means are fastened to the container adjacent the prescored portion so that when the package is flexed, the container breaks on the prescored line releasing the liquid contents into the absorbent.

A further object of the invention is to provide a disposable liquid applicator which is simple in construction and efficient to manufacture.

Other objects and advantages of the present invention will become apparent as the description proceeds. It is to be understood, however, that the invention is not limited to a medication dispenser, and other uses involving various types of liquids may be employed.

BRIEF DESCRIPTION OF THE INVENTION

In accordance with the present invention, a disposable liquid applicator is provided which comprises a container having an elongated body and carrying a liquid to be dispensed. The container has a prescored portion extending transverse the elongated body on one side thereof. Means are provided for sealing the container on another side thereof.

Absorbent means are fastened to the container and overlap the prescored portion. The container and the absorbent means cooperate to cause the liquid to be dispensed into the absorbent means when the container is bent away from the prescored portion and about itself, to release the liquid through the prescored portion and into the absorbent means.

In the illustrative embodiment, the container comprises an elongated plastic blister with the prescored portion extending transverse the entire width of the blister at a generally central location thereof. The sealing means comprises a metal foil that is heat sealed to the plastic blister.

A more detailed explanation of the invention is provided in the following description and claims, and is illustrated in the accompanying drawings.

DETAILED DESCRIPTION OF THE ILLUSTRATIVE EMBODIMENT

Figure 1:
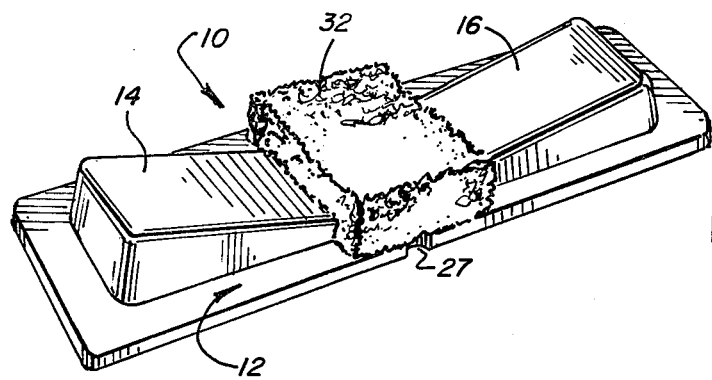
FIG. 1 is a perspective view of a disposable liquid applicator constructed in accordance with the principles of the present invention.

Referring to the drawings, the disposable liquid applicator 10 comprises a vacuum formed container 12. Container 12 has an elongated body and is a blister including a pair of relatively large raised portions 14, 16 which form two liquid receptacles. Large raised portions 14 and 16 are interconnected by a pair of narrow raised portions 18, 20, which provide liquid communication between all of the raised portions 14, 16, 18 and 20.

The blister forming container 12 includes ends 22, 23 and sides 24, 25 which are punched to define centrally located grooves 26, 27 on the opposed sides. A score line 28 transverses the width of container 12 with score line 28 communicating with grooves 26 and 27. Score line 28 provides a centrally located, relatively frangible portion along narrow raised portions 18 and 20. When the container 12 is bent in the manner illustrated in FIG. 6, prescored portion 28 will sever to release the liquid contained within raised portions 14, 16, 18 and 20.

Figure 2:
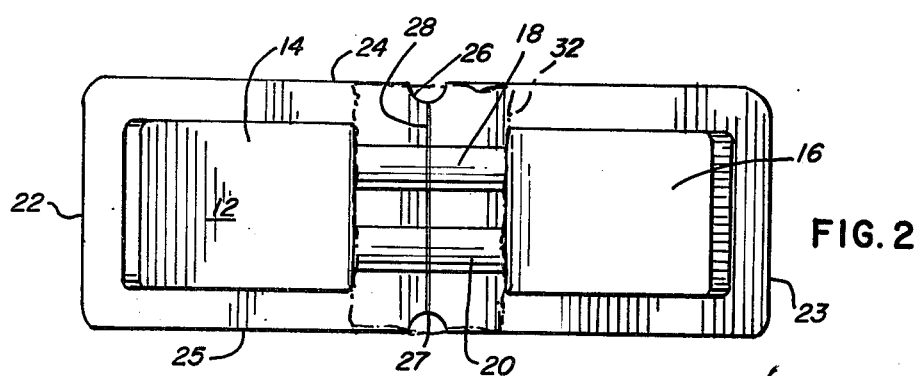
FIG. 2 is a top plan view thereof, with the absorbent sponge being shown in phantom.
Figure 3:
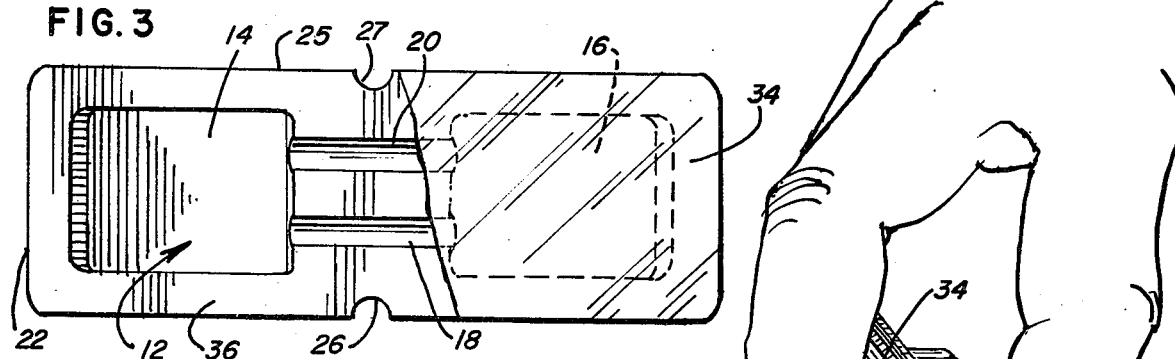
FIG. 3 is a bottom plan view thereof, with the sealing foil being shown broken away for clarity.
Figure 4:
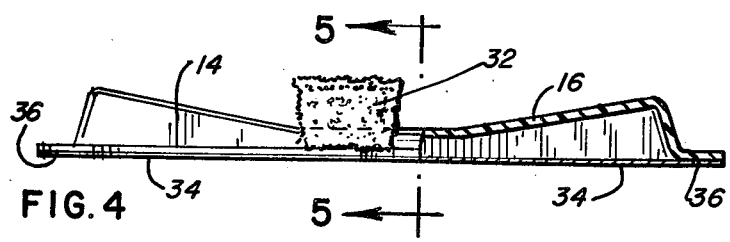
FIG. 4 is a side elevational view thereof.
Figure 5:
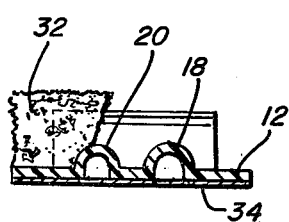
FIG. 5 is a cross-sectional view thereof, taken along the plane of the line 5—5 of FIG. 4.

A sponge 32 formed of suitable absorbent material is fastened to container 20 over prescored portion 28, as illustrated in FIG. 1 and in phantom in FIG. 2. In this manner, when the container is bent to break about the prescored line and the liquid is released, it is released into sponge 32 thereby enabling the device to be used immediately for scrubbing or other purposes for which the liquid is used.

Figure 6:
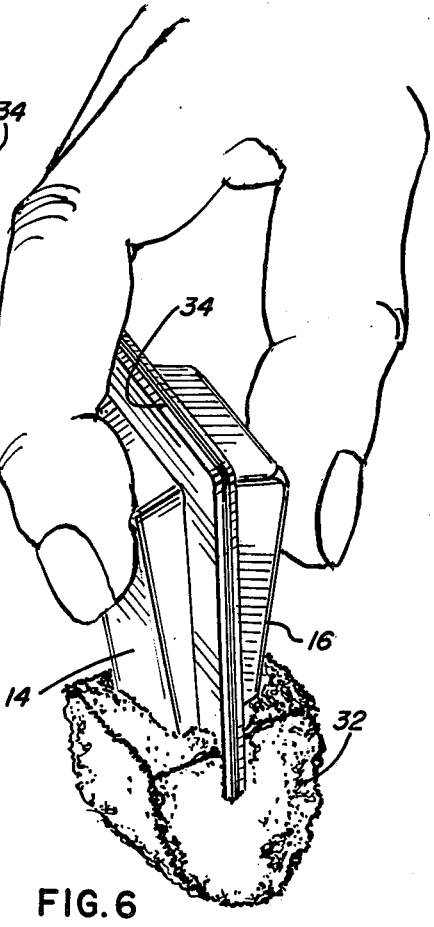
FIG. 6 is a perspective view of the FIG. 1 applicator in use.

After container 12 is filled with the liquid to be dispensed, the container is sealed by means of a planar sheet of metal film 34, such as metal foil, which is heat sealed to the planar underside portion of container 12. In use, the applicator is bent as shown in FIG. 6 to release the liquid into sponge 32.

The device can be manufactured with low cost, high volume production techniques and it results in a relatively inexpensive disposable container, suitable for use in sterilizing a phlebotomy site and in numerous other uses in which a liquid is to be applied via a sponge applicator with the liquid being carried within the device. Although an illustrative embodiment of the invention has been shown and described, it is to be understood that various modifications and substitutions may be made by those skilled in the art without departing from the novel spirit and scope of the invention.

What is claimed is:

1. A disposable liquid applicator which comprises:
   a container having an elongated body and carrying a liquid to be dispensed, said container having a prescored portion extending transverse said elongated body on one side thereof;
   means sealing said container on another side thereof;

absorbent means fastened to said container and overlying said prescored portion; and said container and said absorbent means cooperating to cause the liquid to be dispensed into said absorbent means when said container is bent away from said prescored portion and about itself to release the liquid through said prescored portion and into said absorbent means.

2. A disposable liquid applicator as described in claim 1, said container comprising an elongated plastic blister with said prescored portion extending transverse the entire width of said blister at a generally central location thereof.

3. A disposable liquid applicator as described in claim 2, said sealing means comprising a metal foil that is heat sealed to said plastic blister.

4. A disposable liquid applicator as described in claim 1, said absorbent means comprising a sponge-type material.

5. A disposable liquid applicator as described in claim 1, said container comprising an elongated vacuum formed plastic blister having a prescored portion extending transverse one side thereof, the side of said blister opposite said prescored portion being open initially for filling and being sealed by said sealing means, said sealing means comprising a planar sheet material.

6. A disposable liquid applicator as described in claim 1, said prescored portion extending transverse the entire width of said container.

7. A disposable liquid applicator which comprises:
a container including an elongated vacuum formed plastic blister and carrying a liquid to be dispensed;
said blister having a prescored portion extending transverse the entire width of one side thereof;
the side of said blister opposite said prescored portion being open initially for filling;
means sealing the liquid within said initially open side of said blister, said sealing means comprising a planar sheet material;
absorbent means fastened to said blister and overlying said prescored portion; and
said container and said absorbent means cooperating to cause the liquid to be dispensed into said absorbent means when said container is bent away from said prescored portion and about itself to release the liquid through said prescored portion and into said absorbent means.

8. A disposable liquid applicator as described in claim 7, wherein said sealing means comprises a metal foil that is heat sealed to said plastic blister.

9. A disposable liquid applicator which comprises:
a container having an elongated body and including a pair of relatively large raised portions to form two liquid receptacles interconnected by a narrow raised portion, said raised portions being in communication with each other and containing a liquid to be dispensed;
said narrow raised portion being prescored transverse its width;
means sealing said container;
absorbent means fastened to said container and overlying said prescored narrower portion; and
said container and said absorbent means cooperating to cause the liquid to be dispensed into said absorbent means when said container is bent about itself away from the prescored portion, to release the liquid through the prescored portion of said narrower raised portion and into said absorbent means.

10. A disposable liquid applicator as described in claim 9, in which said two liquid receptacles are interconnected by a pair of parallel, narrow raised portions, each of said narrow raised portions being prescored transverse its width.

* * * * *